(12) United States Patent
Stahmann et al.

(10) Patent No.: US 6,480,740 B2
(45) Date of Patent: Nov. 12, 2002

(54) SAFETY PACING IN MULTI-SITE CRM DEVICES

(75) Inventors: Jeffrey E. Stahmann, Ramsey; Andrew P. Kramer, Stillwater, both of MN (US); Hugh Calkins, Baltimore, MD (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 96 days.

(21) Appl. No.: 09/748,721

(22) Filed: Dec. 26, 2000

(65) Prior Publication Data

US 2002/0082649 A1 Jun. 27, 2002

(51) Int. Cl.[7] .............................................. A61N 1/362
(52) U.S. Cl. ............................................ 607/9; 607/25
(58) Field of Search ...................................... 607/9, 25

(56) References Cited

U.S. PATENT DOCUMENTS

| | | | |
|---|---|---|---|
| 3,835,864 A | 9/1974 | Rasor et al. | 128/419 P |
| 3,943,936 A | 3/1976 | Rasor et al. | 128/419 P |
| 4,091,817 A | 5/1978 | Thaler | 128/419 PG |
| 4,122,294 A | 10/1978 | Frolov | 13/18 R |
| RE30,366 E | 8/1980 | Rasor et al. | 128/419 P |
| 4,332,259 A | 6/1982 | McCorkle, Jr. | 128/786 |
| 4,399,818 A | 8/1983 | Money | 128/419 PG |
| 4,401,119 A | 8/1983 | Herpers | 128/419 PG |
| 4,407,287 A | 10/1983 | Herpers | 28/419 PG |
| 4,408,608 A | 10/1983 | Daly et al. | 128/421 |
| 4,458,677 A | 7/1984 | McCorkle, Jr. | 128/786 |
| 4,592,359 A | 6/1986 | Galbraith | 128/419 R |
| 4,665,925 A | 5/1987 | Millar | 128/663 |
| 4,889,128 A | 12/1989 | Millar | 128/662.06 |
| 4,928,688 A | 5/1990 | Mower | 128/419 PG |
| 4,932,407 A | 6/1990 | Williams | 128/419 D |
| 4,957,111 A | 9/1990 | Millar | 128/662.06 |
| 5,014,696 A | 5/1991 | Mehra | 128/419 D |
| 5,099,838 A | 3/1992 | Bardy | 128/419 D |
| 5,144,960 A | 9/1992 | Mehra et al. | 128/786 |
| 5,165,403 A | 11/1992 | Mehra | 128/419 D |
| 5,167,229 A | 12/1992 | Peckham et al. | 128/421 |
| 5,226,427 A | 7/1993 | Buckberg et al. | 128/772 |
| 5,277,231 A | 1/1994 | Dostalek | 140/106 |
| 5,308,356 A | 5/1994 | Blackshear, Jr. et al. | 606/194 |
| 5,331,966 A | 7/1994 | Bennett et al. | 128/696 |

(List continued on next page.)

FOREIGN PATENT DOCUMENTS

EP 1013303 6/2000 ............ A61N/1/05

OTHER PUBLICATIONS

Stahmann, J.E., et al., "Site Reversion in Cardiac Rhythm Management", *United States Co–Pending Patent Application*, Ser. No. 09/650,658, pp. 1–32, (Filed Aug. 30, 2000).

*Primary Examiner*—Carl Layno
(74) *Attorney, Agent, or Firm*—Schwegman, Lundberg, Woessner & Kluth, P.A.

(57) ABSTRACT

An apparatus and method for providing pacing pulses to a second site when the pacing pulses are inhibited from being provided to a first site. A first cardiac signal and a second cardiac signal are sensed, where both the first and second cardiac signals include indications of cardiac events. A cardiac rate is determined from the cardiac events in one of the first cardiac signal or the second cardiac signal, and pacing pulses are provided to the first cardiac region in order to maintain the cardiac rate at at least a minimum rate value. A pace protection interval starts when a cardiac event is detected in the first cardiac signal. The pace protection interval inhibits delivery of pacing pulses to the first cardiac region. When pacing pulses to the first cardiac region are inhibited because of the pace protection interval, pacing pulses are provided to the second cardiac region at a safety interval timed from the inhibited pacing pulse to the first cardiac region.

26 Claims, 12 Drawing Sheets

U.S. PATENT DOCUMENTS

| | | | |
|---|---|---|---|
| 5,372,125 A | 12/1994 | Lyons | 128/64 D |
| 5,387,233 A | 2/1995 | Alferness et al. | 607/126 |
| 5,405,374 A | 4/1995 | Stein | 607/122 |
| 5,409,469 A | 4/1995 | Schaerf | 604/282 |
| 5,411,524 A | 5/1995 | Rahul | 607/4 |
| 5,423,806 A | 6/1995 | Dale et al. | 606/15 |
| 5,441,504 A | 8/1995 | Pohndorf et al. | 606/129 |
| 5,465,715 A | 11/1995 | Lyons | 128/640 |
| 5,476,498 A | 12/1995 | Ayers | 607/122 |
| 5,540,727 A | 7/1996 | Tockman et al. | 607/18 |
| 5,549,642 A | 8/1996 | Min et al. | 607/5 |
| 5,578,069 A | 11/1996 | Miner, II | 607/126 |
| 5,609,621 A | 3/1997 | Bonner | 607/122 |
| 5,639,276 A | 6/1997 | Weinstock et al. | 606/129 |
| 5,674,217 A | 10/1997 | Wahlstrom et al. | 606/15 |
| 5,674,255 A | 10/1997 | Walmsley et al. | 607/14 |
| 5,700,283 A | 12/1997 | Salo | 607/17 |
| 5,704,351 A | 1/1998 | Mortara et al. | 128/630 |
| 5,713,867 A | 2/1998 | Morris | 604/164 |
| 5,720,768 A | 2/1998 | Verboven-Nelissen | 607/9 |
| 5,744,038 A | 4/1998 | Cham | 210/634 |
| 5,755,761 A | 5/1998 | Obino | 607/122 |
| 5,755,766 A | 5/1998 | Chastain et al. | 607/122 |
| 5,769,875 A | 6/1998 | Peckham et al. | 607/48 |
| 5,772,693 A | 6/1998 | Brownlee | 607/123 |
| 5,776,073 A | 7/1998 | Garfield et al. | 600/546 |
| 5,776,171 A | 7/1998 | Peckham et al. | 607/48 |
| 5,782,879 A | 7/1998 | Rosborough et al. | 607/6 |
| 5,803,928 A | 9/1998 | Tockman et al. | 607/122 |
| 5,814,088 A | 9/1998 | Paul et al. | 607/28 |
| 5,824,032 A | 10/1998 | Belden | 607/126 |
| 5,843,117 A | 12/1998 | Alt et al. | 606/194 |
| 5,871,529 A | 2/1999 | Bartig et al. | 607/122 |
| 5,871,531 A | 2/1999 | Struble | 607/126 |
| 5,902,324 A | 5/1999 | Thompson et al. | 607/9 |
| 5,913,887 A | 6/1999 | Michel | 607/123 |
| 5,922,014 A | 7/1999 | Warman et al. | 607/123 |
| 5,925,073 A | 7/1999 | Chastain et al. | 607/122 |
| 5,931,864 A | 8/1999 | Chastain et al. | 607/128 |
| 5,935,160 A | 8/1999 | Auricchio et al. | 607/122 |
| 5,954,758 A | 9/1999 | Peckham et al. | 607/48 |
| 5,978,707 A | 11/1999 | Krig et al. | 607/14 |
| 5,983,138 A | 11/1999 | Kramer | 607/9 |
| 6,006,137 A | 12/1999 | Williams | 607/119 |
| 6,014,581 A | 1/2000 | Whayne et al. | 600/523 |
| 6,026,328 A | 2/2000 | Peckham et al. | 607/48 |
| 6,027,462 A | 2/2000 | Greene et al. | 600/585 |
| 6,049,732 A | 4/2000 | Panescu et al. | 600/523 |
| 6,055,457 A | 4/2000 | Bonner | 607/126 |
| 6,061,594 A | 5/2000 | Zhu et al. | 607/28 |
| 6,070,104 A | 5/2000 | Hine et al. | 607/123 |
| RE36,765 E | 7/2000 | Mehra | 607/4 |
| 6,106,460 A | 8/2000 | Panescu et al. | 600/300 |
| 6,112,117 A | 8/2000 | KenKnight et al. | 607/5 |
| 6,115,626 A | 9/2000 | Whayne et al. | 600/427 |
| 6,123,456 A | 10/2000 | Sommer et al. | 607/127 |
| 6,129,750 A | 10/2000 | Tockman et al. | 607/125 |
| 6,144,880 A | 11/2000 | Ding et al. | 607/23 |
| 6,148,233 A | 11/2000 | Owen et al. | 607/5 |
| 6,159,237 A | 12/2000 | Alt et al. | 623/1.11 |
| 6,163,725 A | 12/2000 | Peckham et al. | 607/61 |
| 6,256,536 B1 | 7/2001 | Kramer | 607/9 |
| 6,263,242 B1 * | 7/2001 | Mika et al. | 607/9 |
| 6,285,907 B1 | 9/2001 | Kramer et al. | 607/9 |
| 6,370,430 B1 * | 4/2002 | Mika et al. | 607/9 |
| 2001/0016759 A1 | 8/2001 | Kramer et al. | 607/9 |
| 2001/0031993 A1 | 10/2001 | Salo et al. | 607/9 |
| 2001/0041918 A1 | 11/2001 | Baker et al. | 607/9 |

* cited by examiner

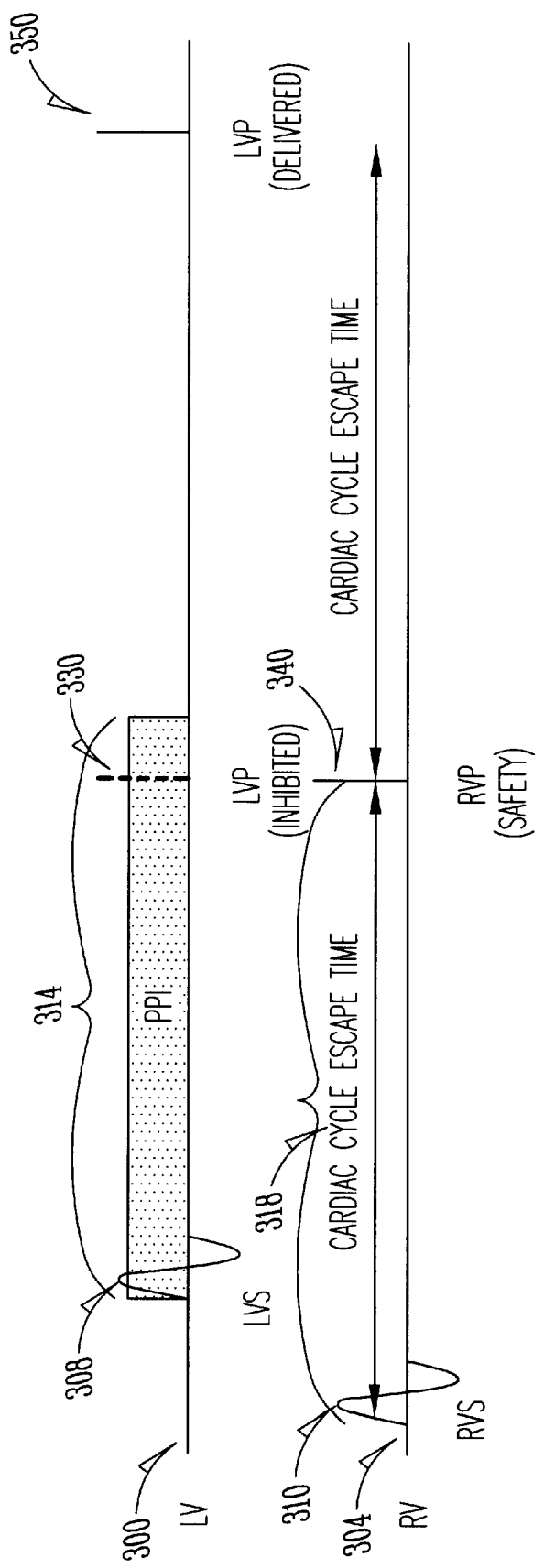

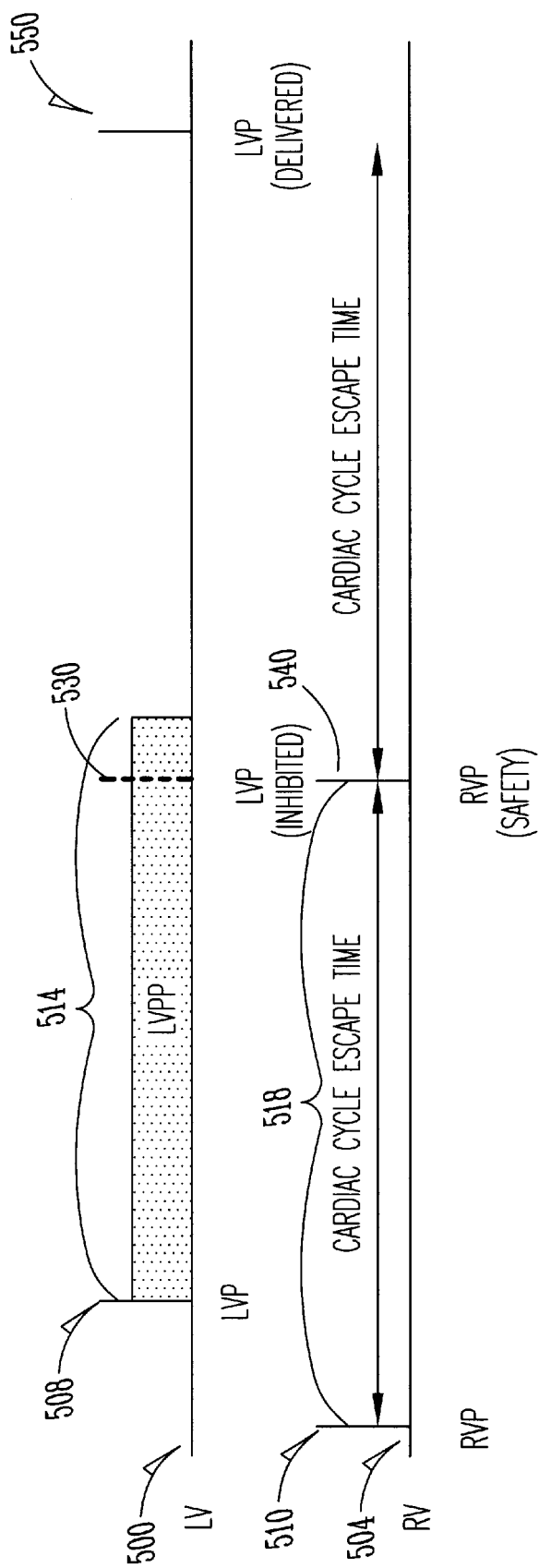

SAFETY PACING IN MULTI-SITE CRM DEVICES

TECHNICAL FIELD

The invention relates generally to cardiac rhythm management systems, and particularly, but not by way of limitation, to a system providing, among other things, reversionary behavior in multi-region pacing therapy.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular lead (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is the treatment of heart failure. In some forms, heart failure can be treated by biventricular coordination therapy that provides pacing pulses to both right and left ventricles, or by biatrial coordination therapy that provides pacing pulses to both the right and left atrium, or other multichamber coordination therapy. Biventricular and biatrial coordination therapy each rely on multiple leads to carry out the coordination therapy of multiple chambers of the heart. In the event of a failure in one or more of the leads (e.g., failure of an electrode), or in the algorithm controlling the coordination therapy, the benefit of coordination therapy may be lost.

As will be seen from the above concerns, there exists a need for improved failure recovery mechanisms in cardiac rhythm management systems used in biventricular and/or biatrial coordination therapy. The above-mentioned problems with failure recovery and other problems are addressed by the various embodiments of the invention and will be understood by reading and studying the following specification.

SUMMARY

The various embodiments of the present subject matter include methods for pacing site redundancy in a cardiac rhythm management system and apparatus capable of carrying out the methods.

The present subject matter includes an apparatus and method where a first cardiac signal and a second cardiac signal are sensed. Both the first and second cardiac signals include indications of cardiac events that can include intrinsic cardiac events or paced cardiac events. A cardiac rate is determined from the cardiac events in one of the first cardiac signal or the second cardiac signal, and pacing pulses are provided to the first cardiac region in order to maintain the cardiac rate at at least a minimum rate value.

A pace protection interval starts when a cardiac event is detected in the first cardiac signal, where the pace protection interval functions to inhibit delivery of pacing pulses to the first cardiac region. In one embodiment, the pace protection interval starts in the first cardiac signal after the intrinsic cardiac event in the first cardiac signal. Alternatively, the pace protection interval starts in the first cardiac signal after the paced cardiac event in the first cardiac signal.

A cardiac cycle escape time interval is then started after either the intrinsic cardiac event is sensed in the second cardiac signal or the paced cardiac event is identified in the first or second cardiac signal. The second cardiac signal is analyzed for an intrinsic cardiac event during the cardiac cycle escape time interval. When the intrinsic cardiac event is not detected in the second cardiac signal during the cardiac cycle escape time interval, the pacing pulse is provided to the second cardiac region at a safety interval timed from the inhibited pacing pulse to the first cardiac region. In one embodiment, the pacing pulse is provided to the second cardiac site at the end of the cardiac cycle escape time interval when the subsequent intrinsic cardiac event is not detected in the second cardiac signal during the cardiac cycle escape time interval. In one embodiment, the pacing pulse is provided to the second cardiac region to maintain the cardiac rate at at least the minimum rate value when the pace protection interval inhibits the pacing pulse to the first cardiac region.

In one embodiment, the pacing pulse is provided to the second cardiac region after the pace protection interval. Alternatively, the pacing pulse is provided to the second cardiac region during, or at the end of, the pace protection interval. In one embodiment, where the pacing pulse is delivered relative the pace protection interval is a function of the safety interval, where the safety interval timed from the inhibited pacing pulse is set in the range of zero (0.0) milliseconds to 300 milliseconds.

This summary is not intended to be exclusive or exhaustive of all embodiments provided by the present application, and further details are found in the detailed description.

BRIEF DESCRIPTION OF THE DRAWINGS

FIG. 3A is an illustration of a first cardiac signal and a second cardiac signal according to the present subject matter;

FIG. 5A is an illustration of a first cardiac signal and a second cardiac signal according to the present subject matter;

DESCRIPTION OF THE EMBODIMENTS

Figure 1:
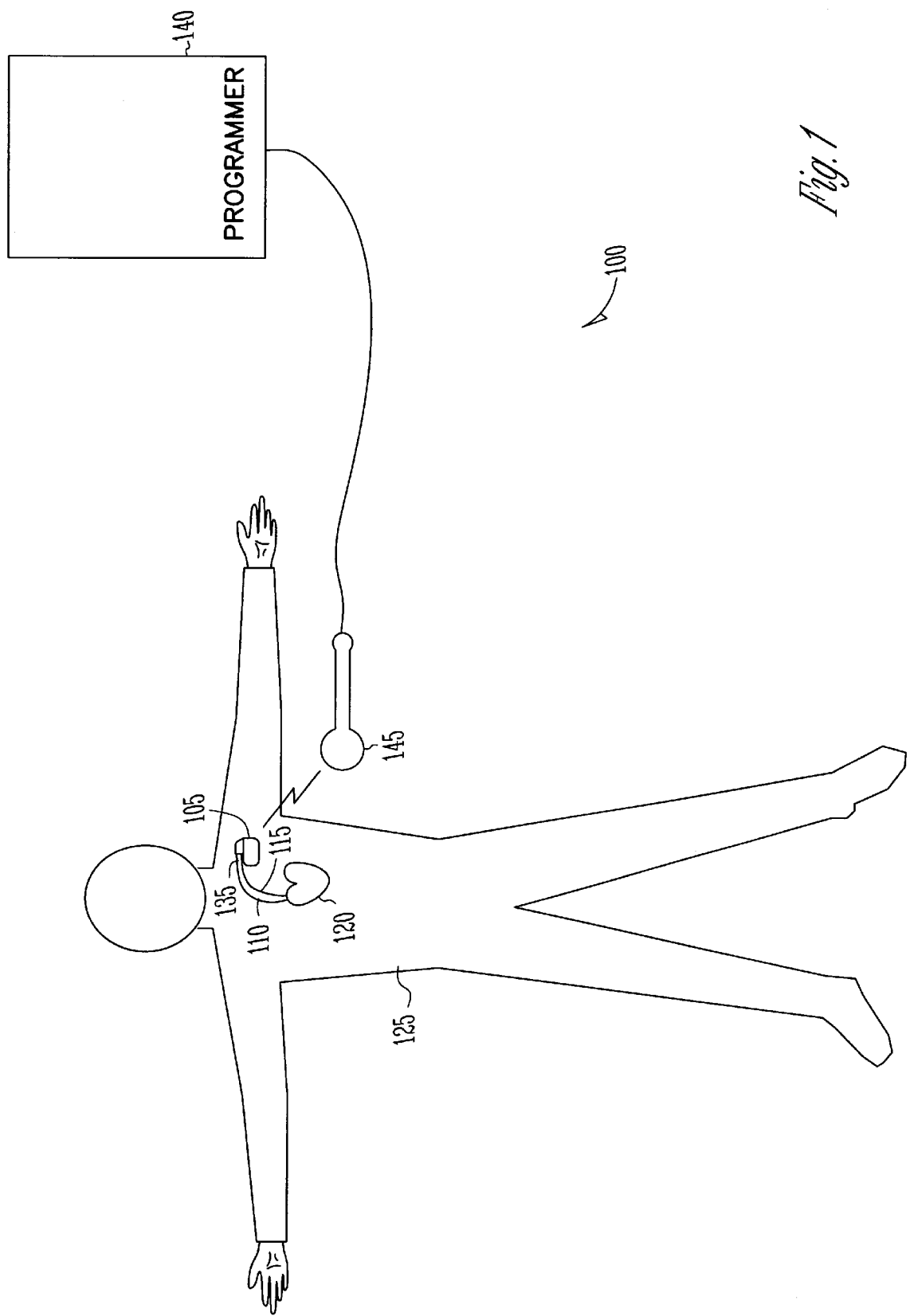
FIG. 1 is a schematic drawing illustrating generally one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the spirit and scope of the invention. The following detailed description is, therefore, not to be taken in a limiting sense, and the scope of the invention is defined by the appended claims and their equivalents.

The various embodiments will generally be discussed in the context of biventricular pacing therapies, having leads coupled to both the right and left ventricles. However, the methods described herein can be adapted to biatrial pacing therapies, having leads coupled to both the right and left atrium, as well as other multichamber pacing therapies, e.g., one atrium/two ventricles, two atriums/two ventricles, etc. Furthermore, the methods described herein can be adapted to unichamber therapies, having multiple lead sites within a single chamber.

The presence of multiple lead sites permits useful reversionary behavior. For example, consider a system in which one lead is implanted in the right ventricle and another lead is implanted adjacent the left ventricle. Suppose that the system was designed to provide pacing pulses only to the left ventricle though the lead implanted adjacent the left ventricle. There are a number of situations in which the implantable signal generator may not deliver therapy through the left ventricular site. These situations will be specifically outlined below. For now, however, should this situation arise in a pacemaker dependent patient, the patient may be asystolic for as long as the device inhibits the pacing therapy to the left ventricle.

A solution to this problem is to use the inherent redundancy provided by the right ventricular lead. The present subject matter allows for a pacing pulse to be delivered to an alternative site when a pacing pulse is inhibited from being delivered to its primary, or typical, site. This allows at least a minimum pacing rate to be maintained even when the pacing pulses are inhibited from being delivered to their primary site.

There are many reasons why a system in which a cardiac signal from both a first cardiac region and a second cardiac region are sensed and analyzed, but only delivers pacing pulses to the first cardiac region, may be unable to deliver the programmed pacing therapy. These can be grouped into two general classes. The first class includes therapy inhibition due to failures and the second class includes therapy inhibition due to normal algorithm behavior. Examples in the first class (failures) include oversensing, lead failure, lead-tissue interface failure and memory failure. These, and other, examples of failures, and how the failures are addressed, are found in copending U.S. patent application Ser. No. 09/650,568 entitled "Site Reversion in Cardiac Rhythm Management" filed on Aug. 30, 2000 that is hereby incorporated by reference in its entirety. Examples of the second class include algorithms that are designed to inhibit pacing during specified time intervals following a sensed or paced cardiac event at a primary pacing site. Since pacing pulses are not delivered in this situation, the patient's cardiac rate may fall below a predetermined minimum value. This is an undesirable situation which the present subject matter addresses.

FIG. 1 is a schematic drawing illustrating, by way of example, but not by way of limitation, one embodiment of portions of a cardiac rhythm management system 100 and an environment in which it is used. In FIG. 1, system 100 includes an implantable signal generator 105 that is coupled by a first cardiac lead 110 and a second cardiac lead 115, or one or more additional leads, to a heart 120 of a patient 125. Implantable signal generator 105 can take the form of an implantable pacemaker or an implantable cardioverter/defibrillator that includes pacing capability. The implantable signal generator 105 is adapted to perform the methods as described herein. System 100 also includes an external programmer 140 that provides for wireless communication with pacemaker 105 using a telemetry device 145. The first cardiac lead 110 and the second cardiac lead 115 each include a proximal end and a distal end, where the distal end of the leads 110 and 115 are implanted in, or on, the heart 120 at a first cardiac region and a second cardiac region, respectively. Each lead includes one or more electrodes, as will be described below, that allow for combinations of either unipolar and/or bipolar sensing and delivery of energy to the heart 120 for pacing, cardioversion and/or defibrillation.

Figure 2:
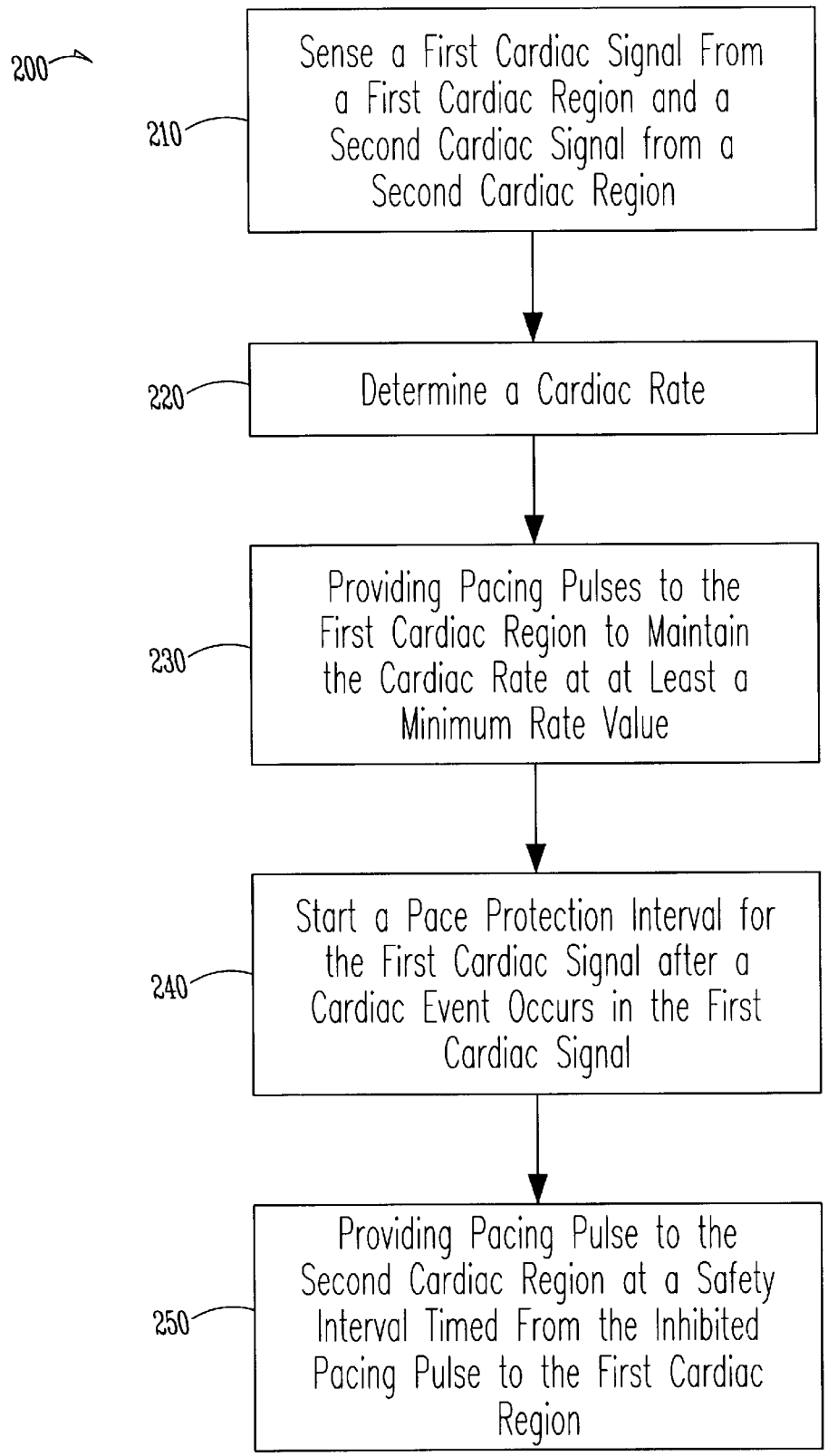
FIG. 2 is a flowchart showing one embodiment of the present subject matter.

FIG. 2 is a flow chart illustrating one embodiment of a method 200 according to the present subject matter. At 210, a first cardiac signal is sensed from a first cardiac region and a second cardiac signal is sensed from a second cardiac region. In one embodiment, the first cardiac signal is sensed from a left ventricular region through the use of one or more electrodes on a cardiac lead. The cardiac lead is positioned adjacent the left ventricle, where the lead is either implanted transvenously (e.g., positioned through the coronary vasculature) or implanted epicardially on the surface of the heart so as to position the one or more electrodes adjacent the left ventricle. In one embodiment, the one or more electrodes sense either unipolar or bipolar cardiac signals from the left ventricular region, as will be described in greater detail below.

Additionally, the second cardiac signal is sensed from a right ventricular region through the use of one or more electrodes on the cardiac lead. The cardiac lead is positioned with its distal end in the right ventricle, where in one embodiment the distal end of the lead is positioned in the apex of the right ventricle. Other locations within the right ventricle are, however, possible for implanting the distal end of the cardiac lead. In one embodiment, the one or more electrodes sense either unipolar or bipolar cardiac signals from the right ventricular region, as will be described in greater detail below. In an alternative embodiment, the first cardiac signal is sensed from a right ventricular chamber and the second cardiac signal is sensed from a left ventricular chamber.

In addition to ventricular locations, other cardiac locations exist from which the first and second cardiac signals can be sensed. For example, the first and second cardiac signals are sensed from left and right atrial chambers, respectively, or from right and left atrial chamber, respectively. Alternatively, the first and second cardiac signals are sensed from two different regions within the same cardiac chamber (e.g., either right atrium or ventricle, or adjacent left atrium or ventricle).

The first cardiac signal and the second cardiac signal each include indications of cardiac events. The type of cardiac event sensed in each of the cardiac signals depends upon the type of electrodes used and the location of the implanted electrodes. Examples of sensed cardiac events include sensed P-waves from atrial depolarization and R-waves and/or QRS-complexes from ventricular depolarizations. From this information, a cardiac rate is determined at 220 from the cardiac events in one of either the first cardiac signal or the second cardiac signal. In one embodiment, the cardiac rate is determined from intrinsic cardiac contractions detected in either the first or second cardiac signal. Alternatively, the cardiac rate is determined from paced cardiac contractions detected in the first or second cardiac signal.

Based on the cardiac rate, at 230 pacing pulses are provided to the first cardiac region to maintain the cardiac rate at at least a minimum rate value. In one embodiment, the minimum rate value is a programmable value and represents the minimum cardiac rate which the implantable signal generator will maintain for the heart. When the heart's own intrinsic rhythm is sufficient to maintain the cardiac rate at the minimum rate value, providing the pacing pulses to the first cardiac region may not be required. Alternatively, when the intrinsic rhythm is insufficient to maintain the cardiac rate at the minimum rate value, pacing pulses are delivered, as necessary, to maintain at least this minimum cardiac rate.

At 240, a pace protection interval is started for the first cardiac signal after a cardiac event occurs in the first cardiac signal. The cardiac events in the first cardiac signal are the result of either a pacing pulse delivered to the first cardiac region or an intrinsic contraction sensed from the first cardiac region or possibly a far-field sense of an intrinsic contraction of the second cardiac region or non-cardiac signals. The pace protection interval is a time interval during which pacing pulses to the first cardiac region are inhibited. In one embodiment, the pace protection interval is a programmable time interval that is set in the range of 200 milliseconds to 500 milliseconds, where 400 milliseconds is a possible value for the pace protection interval.

During the pace protection interval pacing pulses to the first cardiac region are inhibited. In one embodiment, pacing pulses to the first cardiac region are inhibited during a vulnerable time of the cardiac cycle in the first cardiac region. Examples of these vulnerable times include the occurrence of the T-wave in the first cardiac region, where the T-wave occurs during the repolarization of the cardiac tissue in the first region. Pacing pulses delivered to the cardiac tissue during the T-wave can cause an arrhythmia, such as a fibrillation, to occur. Thus, in an effort to avoid inducing an arrhythmia, pacing pulses are inhibited during the pace protection interval.

While pacing pulses to the first cardiac region are inhibited, pacing pulses are not inhibited from being provided to the second cardiac region. At 250, the pacing pulse is provided to the second cardiac region at a safety interval timed from the inhibited pacing pulse to the first cardiac region. In one embodiment, the pacing pulse is provided to the second cardiac region to maintain the cardiac rate at at least the minimum rate value when the pace protection interval inhibits the pacing pulse to the first cardiac region. In one embodiment, the timing of the pacing pulses delivered to the second cardiac region is based on a cardiac cycle escape time interval that is started once a cardiac event is detected in the second cardiac signal. In this example, the pacing pulse is to be provided to the second cardiac region when the cardiac cycle escape time interval expires.

In another embodiment, the timing of the pacing pulses delivered to the second cardiac region is based on a safety interval timed from the inhibited pacing pulse to the first cardiac region.

One possible operating range of the safety interval is the range of zero (0.0) milliseconds to 300 milliseconds which corresponds to the typical range of intrinsic atrioventricular conduction delays. Thus, when the safety interval has a value of 0 milliseconds, the pacing pulse is provided to the second cardiac region at the time when the pacing pulse was to be delivered to the first cardiac region. In this case, the pacing pulse is provided to the second cardiac region during the pace protection interval. In an additional embodiment, the safety interval is programmed such that the pacing pulse is provided to the second cardiac region at the end of the pacing protection interval or after the pace protection interval. Other times and locations relating the inhibited pacing pulse to the first cardiac region for delivering the pacing pulse to the second cardiac region are also possible.

This embodiment has the advantage of timing a pacing pulse to the time of the inhibited pace when that pace is scheduled to occur before a cardiac cycle escape time interval has expired (e.g., in atrial tracking mode after the atrio-ventricular delay). In addition, when the safety interval is programmed to zero (0) milliseconds, the pacing pulse is provided to the second cardiac region at the end of the cardiac cycle escape time interval.

The cardiac cycle escape time interval is an interval, measured in milliseconds, between a cardiac event (e.g., a sensed intrinsic event or a paced event in the second cardiac region) and a subsequently delivered pacing pulse. During the cardiac cycle escape time interval, when an intrinsic cardiac event is sensed in the second cardiac signal, the cardiac cycle escape time interval would terminate and a new cardiac cycle escape time would begin. However, when an intrinsic cardiac event is not sensed in the second cardiac signal during the time interval, a pacing pulse is delivered to the primary pacing location at the end of the cardiac cycle escape time interval. In certain situations, as will be elaborated below, pacing pulses to be delivered at the end of the cardiac cycle escape time interval are inhibited from being delivered to the primary pacing location. To prevent the cardiac rate from falling below the minimum cardiac rate, a "safety" pace (or a back-up pace) is delivered to a secondary pacing location. In the present embodiment, the secondary pacing location is the second cardiac region, while the primary pacing location is the first cardiac region.

FIG. 3A provides an example of the present subject matter. In FIG. 3A, there is shown a first cardiac signal 300 and a second cardiac signal 304. In one embodiment, the first cardiac signal 300 is sensed from a first cardiac region, and the second cardiac signal 304 is sensed from a second cardiac region. As previously discussed, the first and second cardiac regions include combinations of the left ventricle, the right ventricle, the left atrium, and the right atrium. The cardiac regions can also include two regions within, or adjacent to, any of the aforementioned cardiac chambers. For the example in FIG. 3A, the first cardiac signal 300 is sensed from a location adjacent the left ventricle and the second cardiac signal 304 is sensed from the right ventricle.

The example shown in FIG. 3A illustrates an instance when a pacing pulse is delivered to a right ventricular location during an left ventricular only pacing mode. In other words, in this bi-ventricular system, cardiac signals are sensed from both the right and left ventricle, but the primary pacing location is the left ventricle. An intrinsic cardiac contraction is detected in both the first and second cardiac signals, 300 and 304, where the cardiac contraction is shown at 308 in the first cardiac signal 300 and at 310 in the second cardiac signal 304. The intrinsic cardiac contractions 308 and 310 trigger the start of a pace protection interval 314 in the first cardiac signal 300, and a cardiac cycle escape time interval 318 in the second cardiac signal 304, respectively.

Cardiac signals 300 and 304 are then analyzed for the presence of intrinsic cardiac events that occur during the pace protection interval 314 and the cardiac cycle escape time interval 318. In one embodiment, when an intrinsic cardiac event is detected in the right ventricle (i.e., the second cardiac signal 304), the cardiac cycle escape time interval 318 is restarted. If, however, an intrinsic cardiac signal is not detected in the first or second cardiac signals during the cardiac cycle escape time interval 318, a pacing pulse 330 should be delivered to the first cardiac region (the left ventricular region in this example) at the end of the time interval 318. The pacing pulse, however, would be delivered during the pace protection interval 314, and the pacing pulse is therefore inhibited.

With the pacing pulse 330 to the first cardiac region inhibited, there is the possibility that the cardiac rate will fall below the minimum rate value. To prevent the cardiac rate from falling below the minimum cardiac rate, a pacing pulse 340 is delivered not to the first cardiac region, but to the second cardiac region (the right ventricle region in this example). After the pacing pulse 340, the pacing pulses delivered to the first cardiac region is resumed in a next cardiac cycle 350.

In one embodiment, the delay between the cardiac contractions in the right and left ventricles could be due to at least two reasons. First, the contraction in the left ventricle might lag the contraction in the right ventricle, as shown in FIG. 3A, due to a left bundle branch block resulting in a delayed depolarization on the left ventricle. Second, the contraction in the left ventricle might lag the contraction in the right ventricle due to a premature ventricular contraction (PVC) originating in the right ventricle.

Figure 3B:
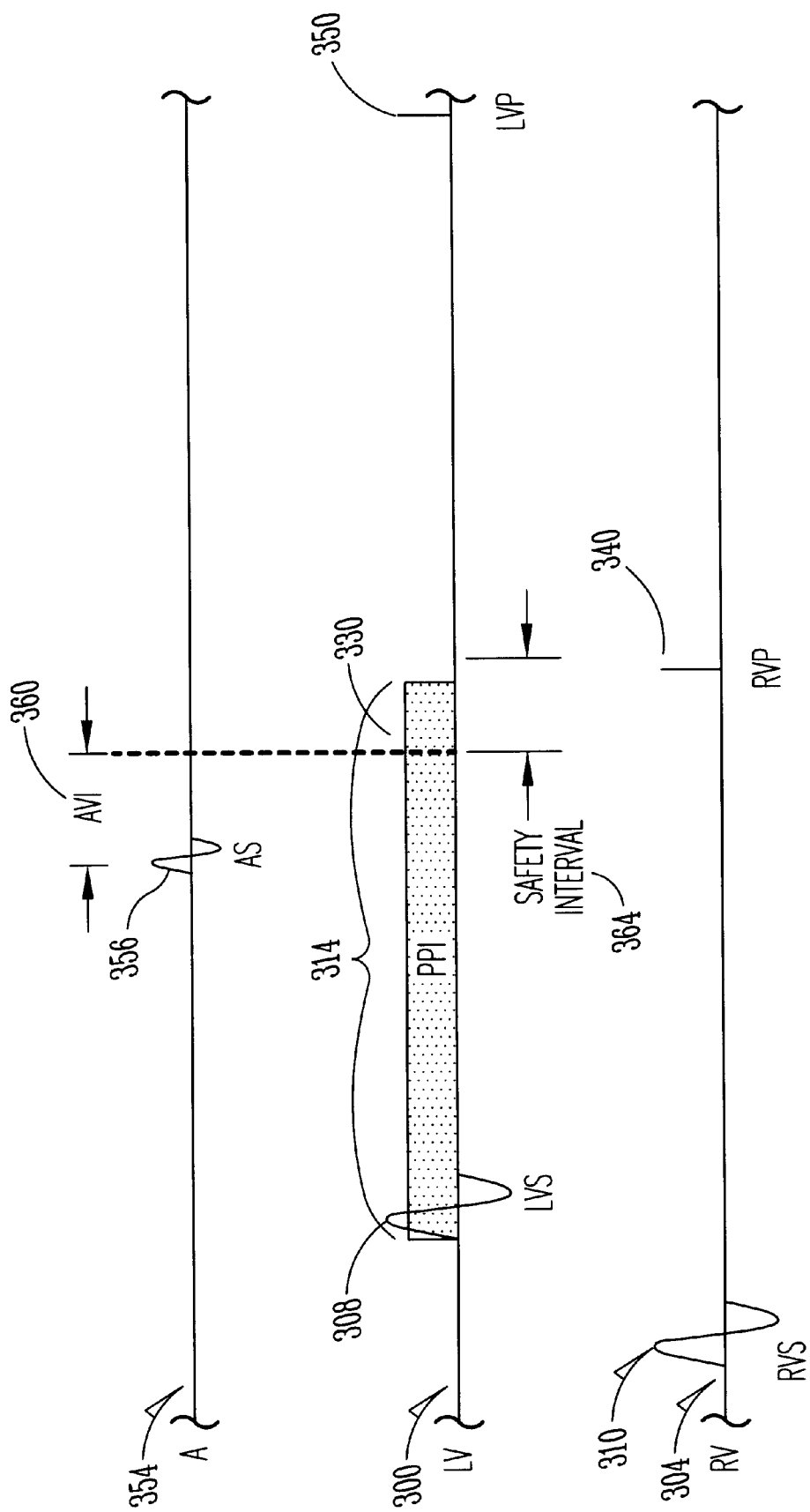
FIG. 3B is an illustration of a first cardiac signal and a second cardiac signal according to the present subject matter.

FIG. 3B provides an additional example of the present subject matter, where the timing of the pacing pulse delivered to the second cardiac region is based on the safety interval from the time when the inhibited pace to the first cardiac region was to have occurred. In FIG. 3B, there is shown the first cardiac signal 300 and the second cardiac signal 304, as previously described. In addition, an atrial cardiac signal 354 is sensed from an atrial location, where the atrial signal 354 includes indications of atrial contractions 356. The example shown in FIG. 3B illustrates a dual chamber implantable pulse generator system, where cardiac signals are sensed from an atrial location and from the right and left ventricles. In this example, the atrial contraction 356 is used to time an atrioventricular interval (AVI) 360. The AVI 360 is the interval between the atrial event 356 and the paced ventricular event. In this example the paced ventricular event should occur at 330, but the pacing pulse 330 is inhibited due to the pace protection interval 314. Instead, pacing pulse 340 is delivered to the second cardiac region. In one embodiment, a safety interval 364 is used to delay the delivery of the pacing pulse 340. This situation allows the pacing pulse 340 to be timed to the inhibited pacing pulse 330 when the inhibited pacing pulse 330 was scheduled to occur before a cardiac cycle escape time interval has expired. After the pacing pulse 340, the pacing pulses delivered to the first cardiac region is resumed in a next cardiac cycle 350.

Figure 3C:
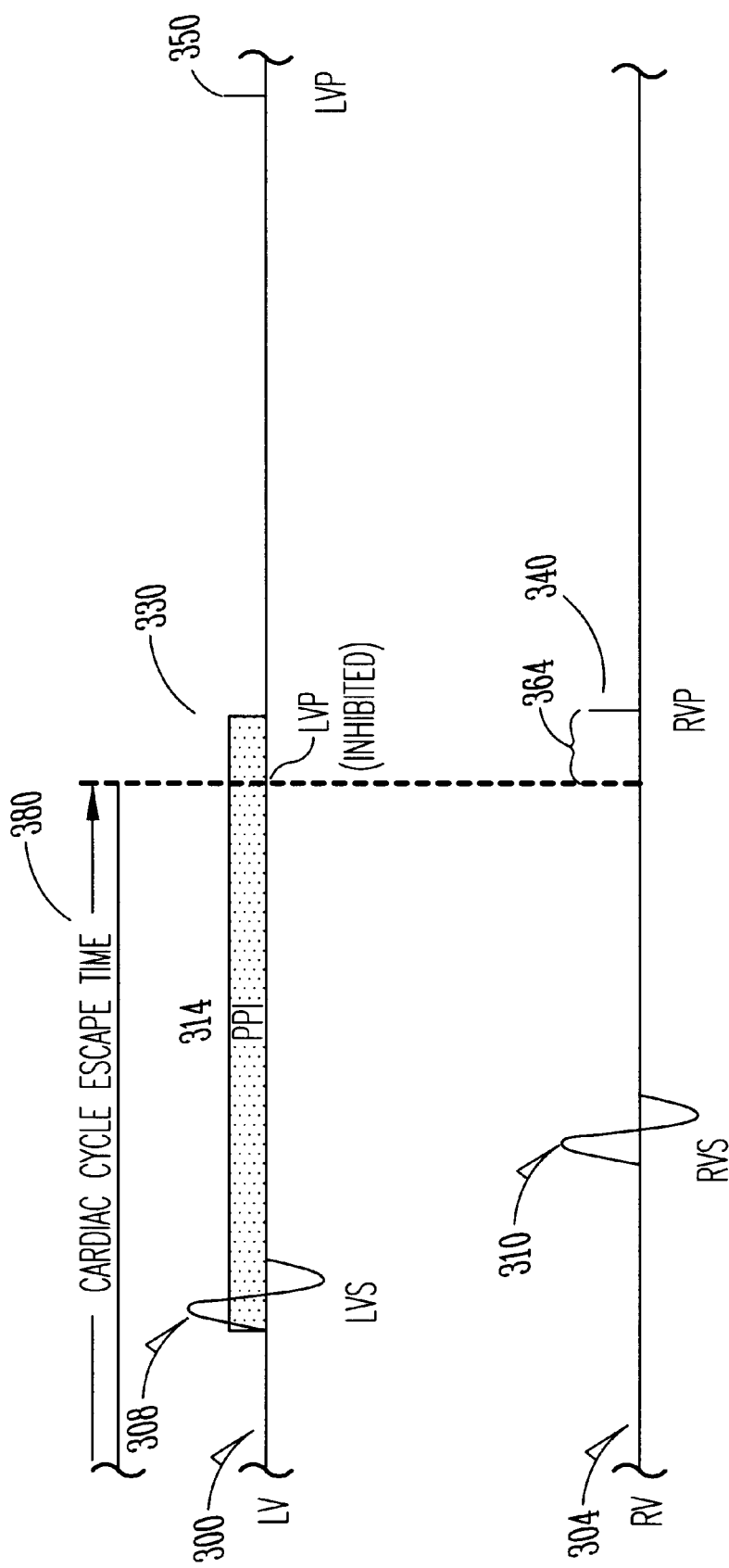
FIG. 3C is an illustration of a first cardiac signal and a second cardiac signal according to the present subject matter.

FIG. 3C provides an additional example of the present subject matter, where the example of FIG. 3C shows an asynchronous pacing mode where only left ventricular events are sensed and right ventricular sensed events are not used to time any pacing events. In FIG. 3C, there is shown the first cardiac signal 300 and the second cardiac signal 304, detected as previously described. In addition, a cardiac cycle escape time interval 380 is shown, where the cardiac cycle escape time interval 380 is started after a right or left ventricular paced event. During the cardiac cycle escape time interval 380, a cardiac contraction is shown at 308 in the first cardiac signal 300 and at 310 in the second cardiac signal 304. In this example, the cardiac contraction 308 detected in the first cardiac signal 300 triggers the start of a pace protection interval 314. However, the cardiac contraction 310 detected in the second cardiac signal 304 is ignored (i.e., the cardiac cycle escape time interval 380 is not reset) due the system operating in an asynchronous pacing mode. One example of this type of mode is a VOO mode, where cardiac contractions in the left ventricular signal are sensed to start the pace protection interval 314, but cardiac signals are not sensed to determine the cardiac cycle time.

In the present example the paced ventricular event should occur at 330 when the cardiac cycle escape time interval 380 expires. However, the pacing pulse 330 is inhibited due to the pace protection interval 314. Instead, pacing pulse 340 is delivered to the second cardiac region. In one embodiment, a safety interval 364 is used to delay the delivery of the pacing pulse 340. After the pacing pulse 340, the pacing pulses delivered to the first cardiac region is resumed in a next cardiac cycle 350.

Figure 4:
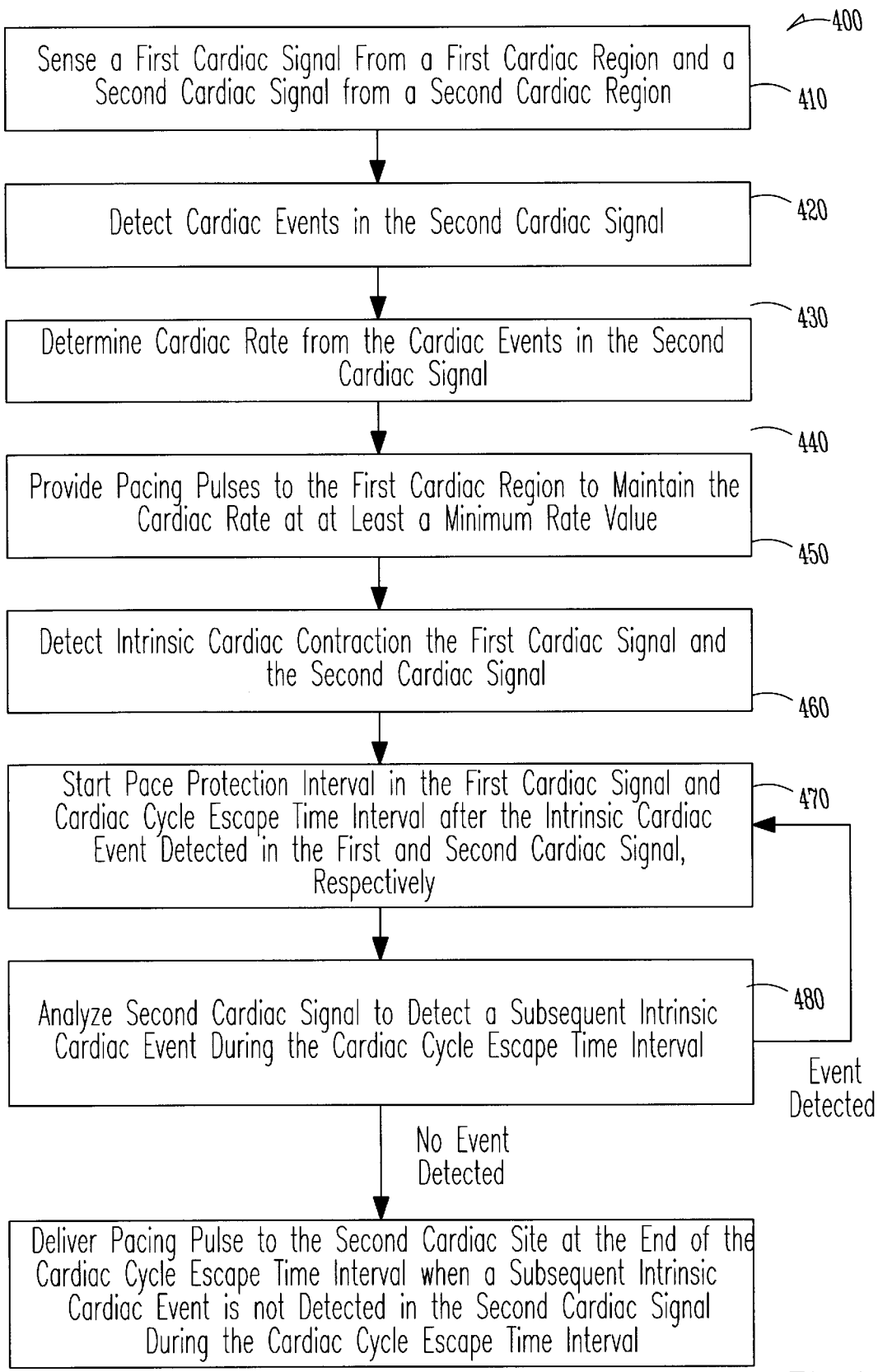
FIG. 4 is a flowchart showing one embodiment of the present subject matter.

FIG. 4 is a flow chart illustrating an embodiment of a method 400 according to the present subject matter. At 410, a first cardiac signal is sensed from a first cardiac region and a second cardiac signal is sensed from a second cardiac region, as discussed for FIG. 2. At 420, intrinsic cardiac events are detected in the sensed second cardiac signal. As previously discussed, intrinsic cardiac events include, but are not limited to, Pwaves as sensed from an atrial location, or R-waves and/or QRS-complexes as sensed from ventricular locations. From this information, a cardiac rate is determined at 430 from the cardiac events in the second cardiac signal. Pacing pulses are provided, if necessary, to the first cardiac region at 440 to maintain the cardiac rate at at least a minimum rate value. However, when the heart's own intrinsic rhythm is sufficient to maintain the cardiac rate at the minimum rate value, providing the pacing pulses to the first cardiac region may not be required.

At 450, an intrinsic cardiac contraction is detected in both the first cardiac signal and the second cardiac signal. At 460, the pace protection interval in the first cardiac signal is started after the intrinsic cardiac event is detected in the first cardiac signal. In addition, a cardiac cycle escape time interval is started after the intrinsic cardiac event is detected in the second cardiac signal. As previously mentioned, the pace protection interval is a programmable time interval that is set in the range of 200 milliseconds to 500 milliseconds, where 400 milliseconds is a possible value for the pace protection interval. In one embodiment, the cardiac cycle escape time interval is also a programmable time interval in the range of 340 to 2000 milliseconds.

At 470, the second cardiac signal is analyzed to detect a subsequent intrinsic cardiac event in the second cardiac signal during the cardiac cycle escape time interval. When an intrinsic cardiac event is detected in the second cardiac signal, the cardiac cycle escape time interval is started again by returning to 460. When a subsequent intrinsic cardiac event is not detected in the second cardiac signal during the cardiac cycle escape time interval, however, a pacing pulse is delivered to the second cardiac site at the end of the cardiac cycle escape time interval, as shown at 480.

FIG. 5A provides an additional example of the present subject matter. In FIG. 5A, there is shown a first cardiac signal 500 and a second cardiac signal 504. In one embodiment, the first cardiac signal 500 is sensed from a first cardiac region, and the second cardiac signal 504 is sensed from a second cardiac region. As previously discussed, the first and second cardiac regions include combinations of the left ventricle, the right ventricle, the left atrium, and the right atrium. The cardiac regions can also include two regions within, or adjacent to, any of the aforementioned cardiac chambers. For the example in FIG. 5A, the first cardiac signal 500 is sensed from a location adjacent the left ventricle and the second cardiac signal 504 is sensed from the right ventricle.

The example shown in FIG. 5A illustrates an instance when a pacing pulse is delivered to a right ventricular location during an left ventricular only pacing mode. In other words, in this bi-ventricular system, cardiac signals are sensed from both the right and left ventricle, but the primary pacing location is the left ventricle. As the cardiac signals are being sensed, a paced cardiac event is identified in each of the first and second cardiac signals, 500 and 504, where the paced cardiac event in the first cardiac signal 500 is shown at 508 and the paced cardiac event in the second cardiac signal 504 is shown at 510. The sensed paced cardiac events 508 and 510 trigger the start of a pace protection interval 514 in the first cardiac signal 500, and a cardiac cycle escape time interval 518 in the second cardiac signal 504.

Cardiac signals 500 and 504 are then analyzed for the presence of intrinsic cardiac events that occur during the pace protection interval 514 and the cardiac cycle escape time interval 518. In one embodiment, when an intrinsic cardiac event is detected in the right ventricle (i.e., the second cardiac signal 504), the cardiac cycle escape time interval 518 is restarted. If, however, an intrinsic cardiac signal is not detected in the first or second cardiac signals during the cardiac cycle escape time interval 518, a pacing pulse 530 should be delivered to the first cardiac region (the left ventricular region in this example) at the end of the time interval 518. The pacing pulse, however, would be delivered during the pace protection interval 514, and the pacing pulse is therefore inhibited.

With the pacing pulse 530 to the first cardiac region inhibited, there is the possibility that the cardiac rate will fall below the minimum rate value. To prevent the cardiac rate from falling below the minimum cardiac rate, a pacing pulse 540 is delivered not to the first cardiac region, but to the second cardiac region (the right ventricle region in this example). After the pacing pulse 540, the pacing pulses delivered to the first cardiac region are resumed at 550 in a next cardiac cycle.

In one embodiment, FIG. 5A illustrates an example where a pacing pulse is invoked when a biventricular cardiac management system is transitioning from a biventricular pacing mode with a positive left ventricular offset (i.e., the pacing pulse to the left ventricle follows the pacing pulse delivered to the right ventricle by a set time interval) to a left ventricle only pacing mode. The paced left ventricular and right ventricular events trigger the pace protection interval and the cardiac cycle escape time interval, as previously discussed. As no intrinsic cardiac events were sensed during the pace protection interval and the cardiac cycle escape time interval, a pacing pulse 540 was delivered to the second cardiac region (the right ventricular region in this instance). The transition to the left ventricular only pacing mode then takes place with the pacing pulse delivered at 550 to start the next cardiac cycle.

Figure 5B:
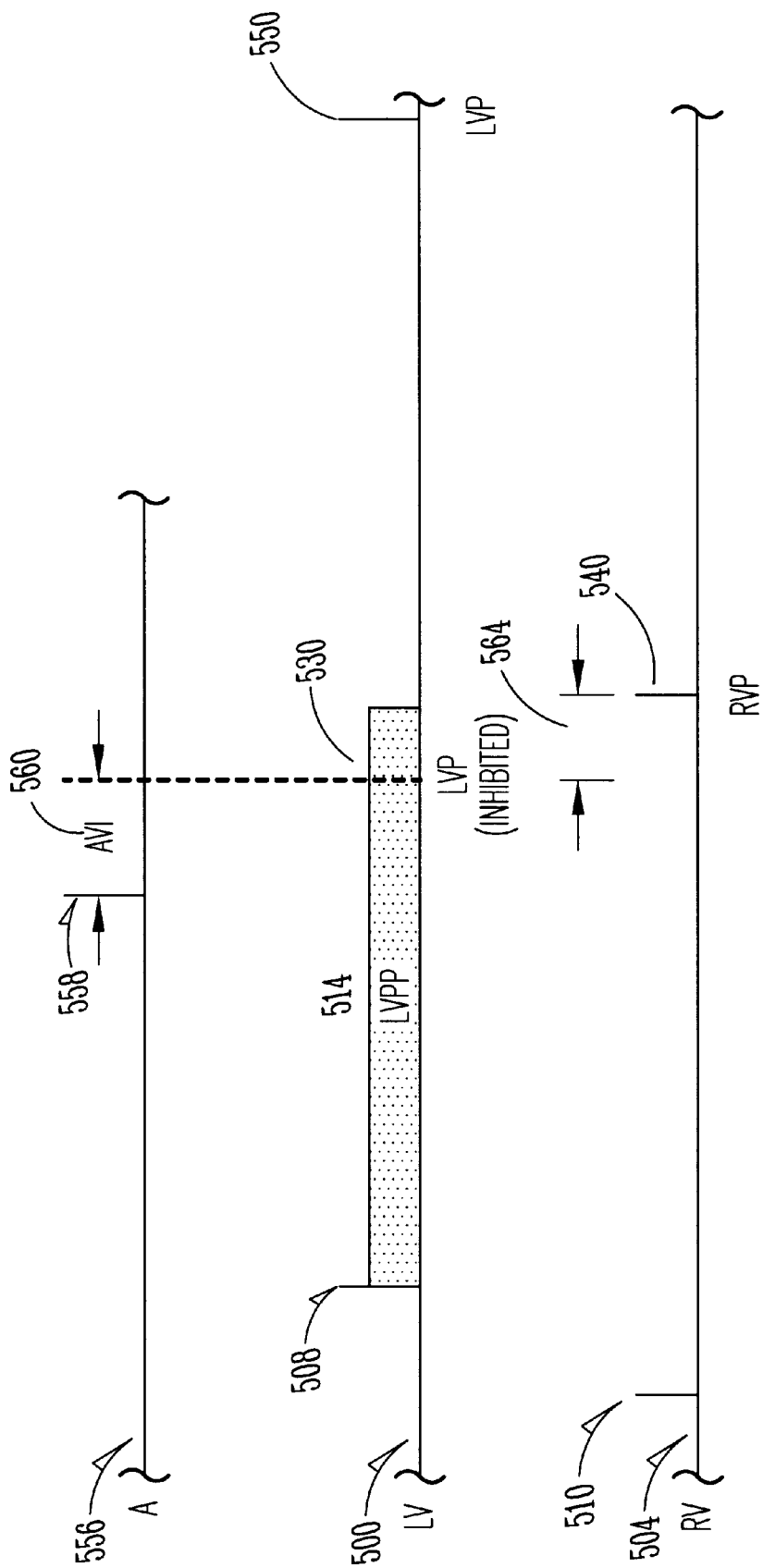
FIG. 5B is an illustration of a first cardiac signal and a second cardiac signal according to the present subject matter.

FIG. 5B provides an additional example of the present subject matter, where the timing of the pacing pulse delivered to the second cardiac region is based on the safety interval from the time when the inhibited pace to the first cardiac region was to have occurred. FIG. 5B illustrates an example where a pacing pulse is invoked when a biventricular cardiac management system is transitioning from a fixed-rate pacing mode (i.e., where pacing rate is independent of the heart's intrinsic rate) to an atrial tracking mode (where pacing follows the intrinsic atrial rate). In FIG. 5B, there is shown the first cardiac signal 500 and the second cardiac signal 504, as previously described. In addition, an atrial cardiac signal 556 is sensed from an atrial location, where the atrial signal 556 includes indications of a paced atrial event 558. The example shown in FIG. 5B illustrates a dual chamber implantable pulse generator system, where cardiac signals are sensed from an atrial location and from the right and left ventricles. In this example, the paced atrial event 558 is used to time an atrioventricular interval (AVI) 560. The AVI 560 is the interval between the paced atrial event 558 and the paced ventricular event. In this example the paced ventricular event should occur at 530, but the pacing pulse 530 is inhibited due to the pace protection interval 514. Instead, pacing pulse 540 is delivered to the second cardiac region. In one embodiment, a safety interval 564 is used to delay the delivery of the pacing pulse 540. This situation allows the pacing pulse 540 to be timed to the inhibited pacing pulse 530 when the inhibited pacing pulse 530 was scheduled to occur before a cardiac cycle escape time interval has expired. After the pacing pulse 540, the pacing pulses delivered to the first cardiac region is resumed in a next cardiac cycle 550.

Figure 6:
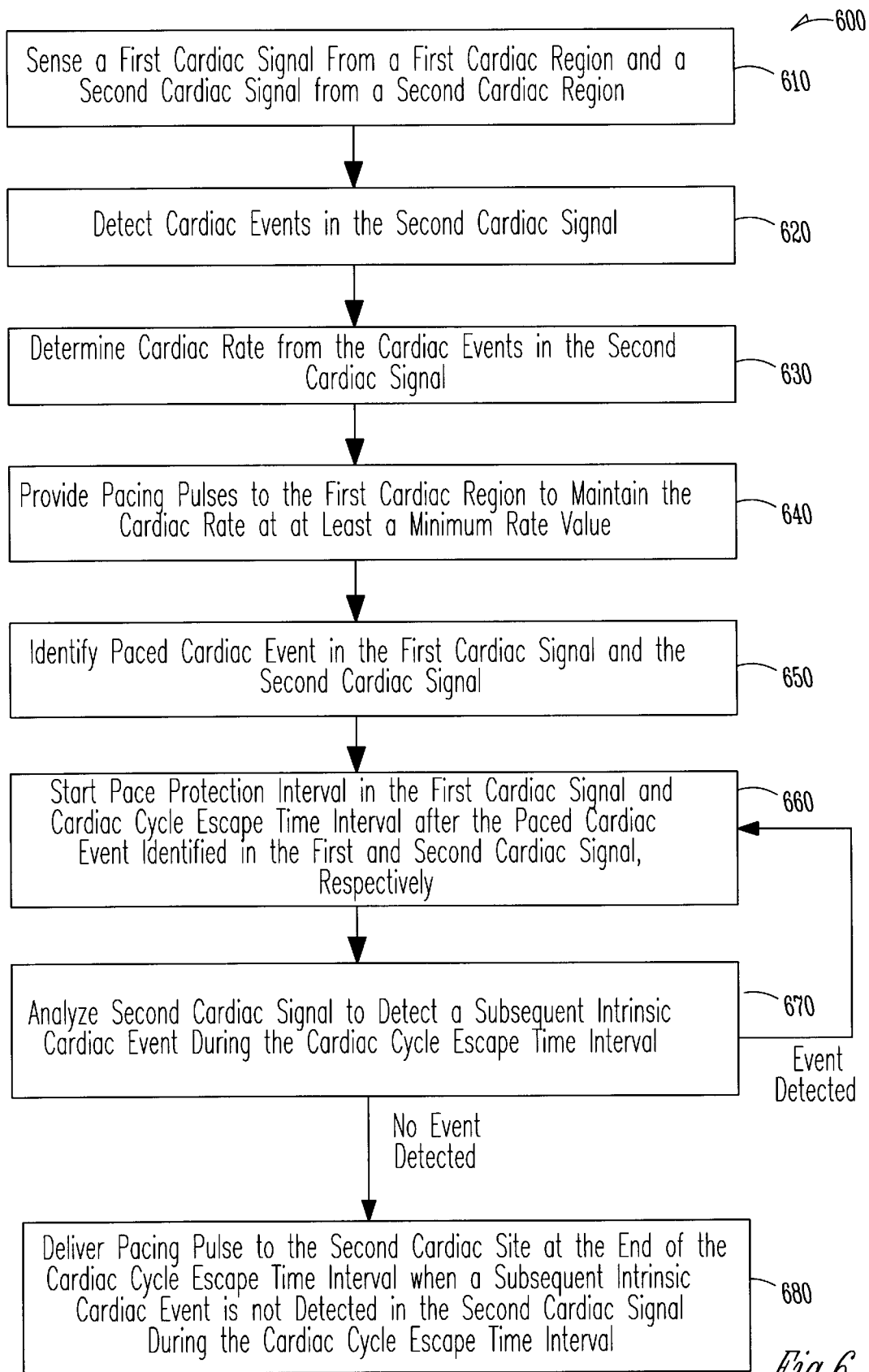
FIG. 6 is a flowchart showing one embodiment of the present subject matter.

FIG. 6 is a flow chart illustrating an embodiment of a method 600 according to the present subject matter. At 610, a first cardiac signal is sensed from a first cardiac region and a second cardiac signal is sensed from a second cardiac region, as discussed for FIG. 2. At 620, intrinsic cardiac events are detected in the sensed second cardiac signal. As previously discussed, intrinsic cardiac events include, but are not limited to, P-waves as sensed from an atrial location, or R-waves and/or QRS-complexes as sensed from ventricular locations. From this information, a cardiac rate is determined at 630 from the cardiac events in the second cardiac signal. Pacing pulses are provided, if necessary, to the first cardiac region at 640 to maintain the cardiac rate at at least a minimum rate value. However, when the heart's own intrinsic rhythm is sufficient to maintain the cardiac rate at the minimum rate value, providing the pacing pulses to the first cardiac region may not be required.

At 650, a paced cardiac event is identified in both the first cardiac signal and the second cardiac signal. At 660, the pace protection interval in the first cardiac signal is started after the paced cardiac event is identified in the first cardiac signal. In addition, a cardiac cycle escape time interval is started after the paced cardiac event is identified in the second cardiac signal. At 670, the second cardiac signal is analyzed to detect a subsequent intrinsic cardiac event in the second cardiac signal during the cardiac cycle escape time interval. When an intrinsic cardiac event is detected in the second cardiac signal, the cardiac cycle escape time interval is started again by returning to 660. When a subsequent intrinsic cardiac event is not detected in the second cardiac signal during the cardiac cycle escape time interval, however, a pacing pulse is delivered to the second cardiac site at the end of the cardiac cycle escape time interval, as shown at 680.

In addition to the embodiments described above, the location of the first cardiac region and the second cardiac region can be reversed. Thus, the first cardiac signal is sensed from the right ventricle and the second cardiac signal is sensed from the left ventricle. Signal processing and analysis occur as described, but with the first cardiac region being the right ventricle and the second cardiac region being the left ventricle. In this embodiment, safety paces would be delivered to the left ventricle instead of the right ventricle.

A still further example of a failure indication can be based on multiple site cross-checking. Excitatory heart tissue naturally propagates electrical activation from one region to another (conduction) as part of its function to generate coordinated contraction within a heart chamber and between left and right chambers of the heart. With a multisite design, multiple leads and/or electrodes are placed within a single heart chamber and/or in both left and right chambers. Due to natural electrical propagation in heart tissue, activation sensed or initiated by pacing at one site will be followed after a predictable conduction delay by sensed activation at another site. Thus, verification of pace capture or sensed activation at one site can be cross-checked by sensing conducted events at another site. For example, if paced capture occurs at a primary site, activation will be sensed at a second site after a conduction delay dependent largely on the distance separating the two sites. If activation is not sensed at the second site within an expected conduction delay window, a failed capture condition is detected at the pacing site and site reversion could occur for a backup pace or for pacing on subsequent cardiac cycles. As another example, if activation is detected by sensing at a primary site, a paired activation will be detected at a second sensing site either just earlier or just later than at the primary site due to conduction. If activation is not detected at the second sensing site within the expected conduction delay window before and/or after detection at the primary site, the detection at the primary site may be due to a failure condition (e.g., sensed noise, oversensing) and sensing site reversion can occur.

Figure 7:
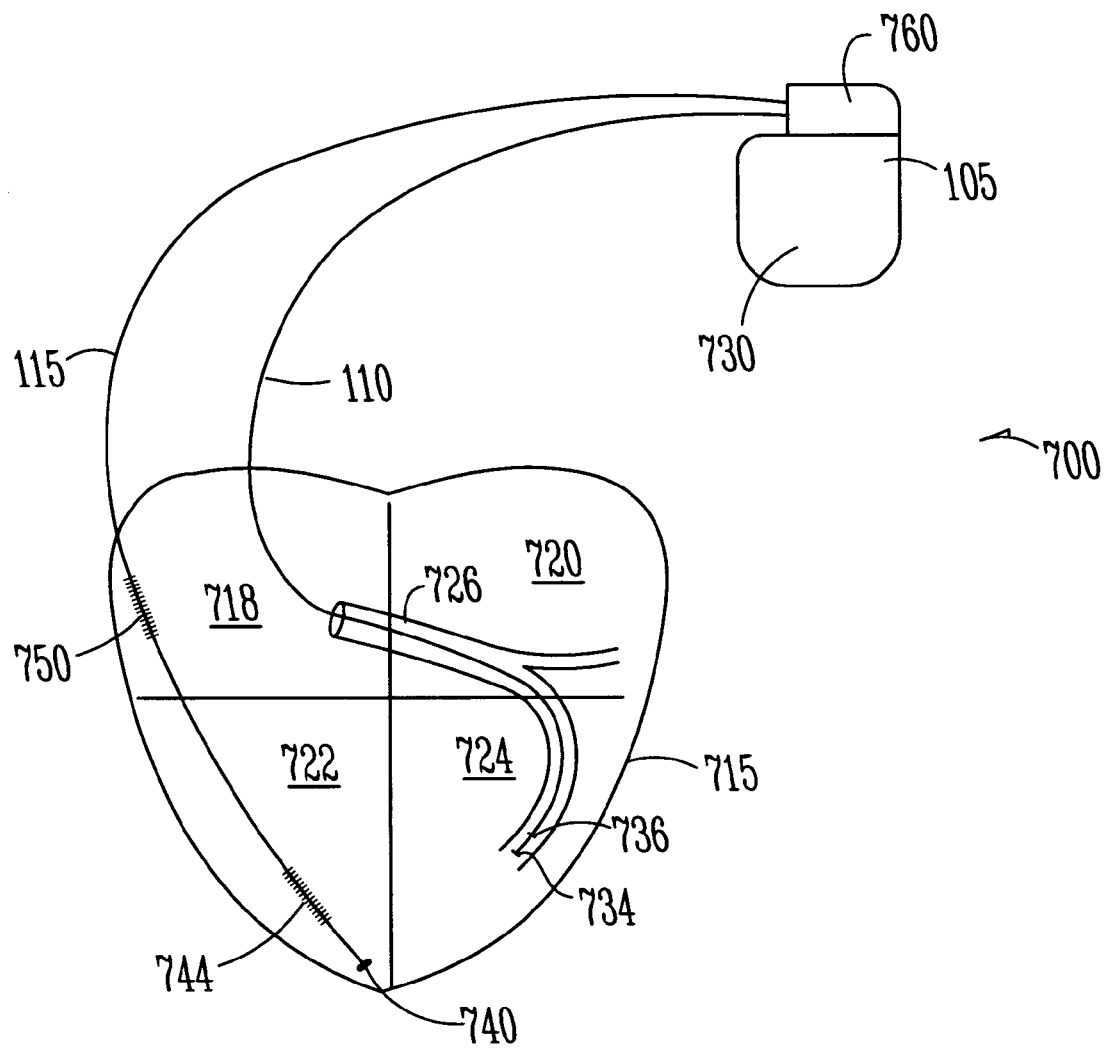
FIG. 7 is a schematic drawing illustrating one embodiment of a cardiac rhythm device coupled by leads to a heart.

FIG. 7 is a schematic drawing illustrating, by way of example, but not by way of limitation, one embodiment of an apparatus 700 that incudes a signal generator 105 coupled by leads 110 and 115 to a heart 715. In one embodiment, lead 110 has at least a first sensing/pacing electrode adapted for connection to the signal generator 105, and lead 115 has a second sensing/pacing electrode also adapted for connection to the signal generator 105. The heart 715 includes a right atrium 718, a left atrium 720, a right ventricle 722, a left ventricle 724, and a coronary sinus 726 extending from right atrium 718. In one such embodiment, the apparatus 700 provides biventricular coordination therapy to coordinate right ventricular and left ventricular contractions, such as for congestive heart failure patients. The system 700 also contains control circuitry within housing 730 that receives the cardiac signals and performs the present subject matter.

In one embodiment, lead 110 is shown with the first sensing/pacing electrode 734 along with an additional sensing/pacing electrode 736. Lead 110 is shown inserted through coronary sinus 726 and into the great cardiac vein so that electrodes 734 and 736 are adjacent the left ventricle 724, where the electrodes 734 and 736 are used to sense intrinsic heart signals and provide one or more coordination paces pulses. In one embodiment, electrodes 734 and 736 are ring electrodes that partially or completely surround lead 110. Alternatively, electrode 736 is a ring electrode and electrode 734 is a tip electrode. In an additional embodiment, lead 110 also includes an additional electrode positioned proximal electrodes 734 and 736, where the additional electrode can be used in combination with electrodes 734 and 736 to provide bipolar and unipolar pacing and sensing from the left ventricular lead 110.

Lead 115 is shown with the second sensing/pacing electrode 740, along with a first defibrillation coil electrode 744 and a second defibrillation coil electrode 750. The second sensing/pacing electrode 740 and the first defibrillation coil electrode 744 are shown disposed in, around, or near the right ventricle 722, for delivering sensing signals and/or delivering pacing therapy. The second defibrillation coil electrode 750 is positioned proximal the first defibrillation coil electrode 744 so as to position the second defibrillation coil electrode 750 at least partially in the right atrium 718. The first and second defibrillation coil electrodes 744 and 750 are then used to deliver atrial and/or ventricular cardioversion/defibrillation therapy to heart 715. In addition, the housing 730 of the signal generator 105 is used as an optional electrode in sensing cardiac signals (unipolar signals sensed between the and delivering electrical energy to the heart in conjunction with any of the aforementioned electrodes). In addition, the apparatus 700 further includes an atrial lead, where the atrial lead includes at least one pace/sense electrode to allow for an atrial cardiac signal to be sensed and for atrial cardiac events to be sensed. The atrial signal is then used in the present subject matter in conjunction with dual chamber devices, as described in FIGS. 3B and 5B.

In FIG. 7, device 105 includes components, such as the electronic control circuitry, enclosed in the hermetically-sealed housing 730. Additional electrodes may be located on the housing 730, may be the housing 730 itself, may be on an insulating header 760, or on other portions of device 105, for providing unipolar or bipolar pacing/sensing and/or defibrillation energy in conjunction with the electrodes disposed on or around heart 715. Other forms of electrodes include meshes and patches which may be applied to portions of heart 715 or which may be implanted in other areas of the body to help "steer" electrical currents produced by device 105. The present method and apparatus will work in a variety of configurations and with a variety of electrical contacts or "electrodes."

Figure 8:
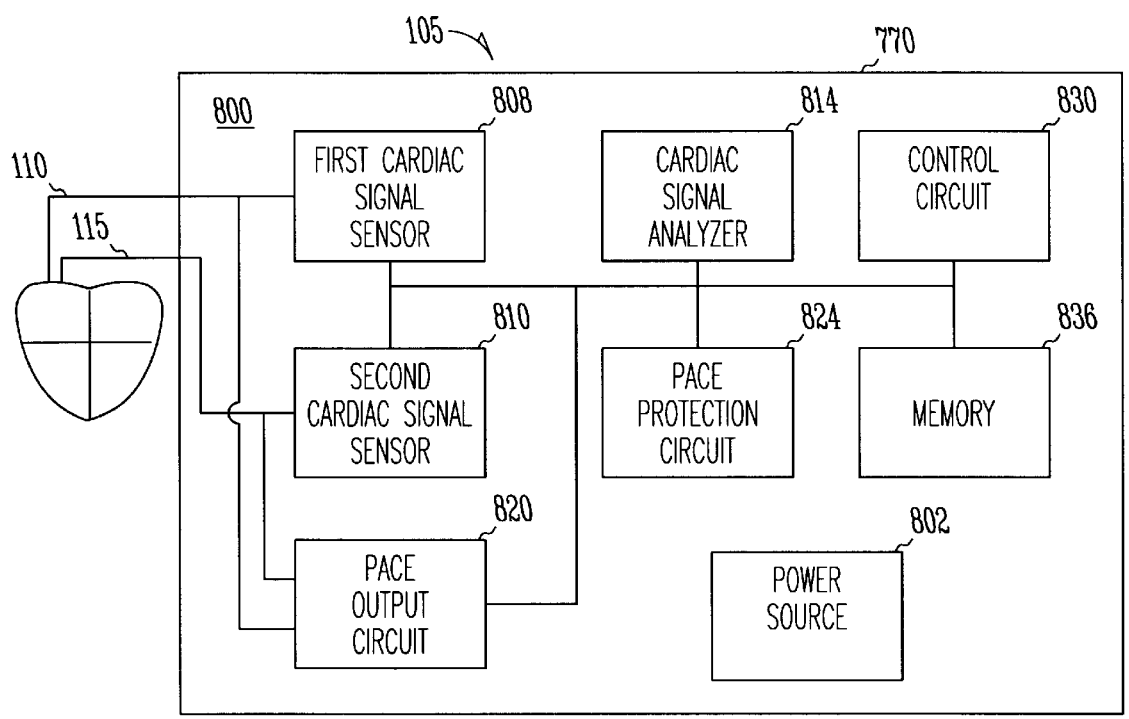
FIG. 8 is a schematic diagram illustrating generally one embodiment of portions of a cardiac rhythm management device coupled to a heart.

FIG. 8 is a schematic diagram illustrating generally, by way of example, but not by way of limitation, one embodiment of control circuitry 800 of the signal generator 105. The signal generator 105, as shown in FIG. 8, includes a power source 802, a first cardiac signal sensor 808, a second cardiac signal sensor 810, a cardiac signal analyzer 814, a pacing output circuit 820, a pace protection circuit 824 and a control circuit 830. In one embodiment, the control circuit 830 incorporates a microprocessor for controlling the signal generator 105. In one embodiment, the function of the pace protection circuit 824 is implemented in software within control circuit 830. In addition, the pace protection interval can also be implemented in software within the control circuit 830.

The first cardiac signal sensor 808 is coupled to the first sensing/pacing electrode on the first cardiac lead 110. In one embodiment, the first cardiac signal sensor 808 uses the first sensing/pacing electrode, along with the additional electrode on 110 or the housing 770, to sense the first cardiac signal as previously described. As discussed, the first cardiac signal is either a unipolar cardiac signal or a bipolar cardiac signal, depending upon the electrodes used in sensing the signal. The second cardiac signal sensor 810 is coupled to the second sensing/pacing electrode on the second cardiac lead 115. In one embodiment, the second cardiac signal sensor 810 uses the second sensing/pacing electrode 740, along with the first defibrillation coil electrode 744 or the housing 770, to sense the second cardiac signal as previously described. As discussed, the second cardiac signal is either a unipolar cardiac signal or a bipolar cardiac signal, depending upon the electrodes used in sensing the signal.

The cardiac signal analyzer 814 receives both the first cardiac signal and the second cardiac signal. The cardiac signal analyzer 814 determines a cardiac rate from the cardiac events in one of the first cardiac signal or the second cardiac signal, as previously discussed. Based on the cardiac rate, the pacing output circuit 820, under the control of the control circuit 830, provides pacing pulses to the first sensing/pacing electrode and the second sensing/pacing electrode to maintain the cardiac rate at at least the minimum rate value. In one embodiment, the minimum rate value is a programmable value that is stored in a memory 836 of the control circuitry 800.

In one embodiment, the cardiac signal analyzer 814 detects intrinsic or identifies paced cardiac event in the first and second cardiac signals. When this occurs, the pace protection circuit 824 starts a pace protection interval in the first cardiac signal, as previously described. The pace protection circuit 824 also starts the cardiac cycle escape time interval after the intrinsic or paced cardiac event is sensed or identified in the second cardiac signal, as previously described. The pace protection circuit 824 then inhibits pacing pulses from the pacing output circuit 820 to the first cardiac region during the pace protection interval.

The cardiac signal analyzer 814 also senses subsequent intrinsic cardiac events in the second cardiac signal during the cardiac cycle escape time interval. When a subsequent intrinsic cardiac event is not detected in the second cardiac signal, the pace protection circuit 824 causes the pacing output circuit 820 to provide a pacing pulse to the second sensing/pacing electrode at the safety interval timed from the inhibited pacing pulse to the first cardiac region. As previously mentioned, the safety interval is programmed in the range of zero (0.0) milliseconds to 300 milliseconds. The safety interval allows the pacing pulse to be provided to the second cardiac region either during the pace protection interval, which includes at the end of the pace protection interval, or after the pace protection interval has ended.

As previously described, one reason for providing the pacing pulse to the second cardiac region is to maintain the cardiac rate at at least the minimum rate value. In addition to providing pacing pulses to the second sensing/pacing electrode, the pace protection circuit 824 causes the pacing output circuit 820 to provide a pacing pulse to the first sensing/pacing electrode to maintain the cardiac rate at at least the minimum rate value when the pace protection circuit 824 does not inhibit the pacing pulse to the first sensing/pacing electrode.

Figure 9:
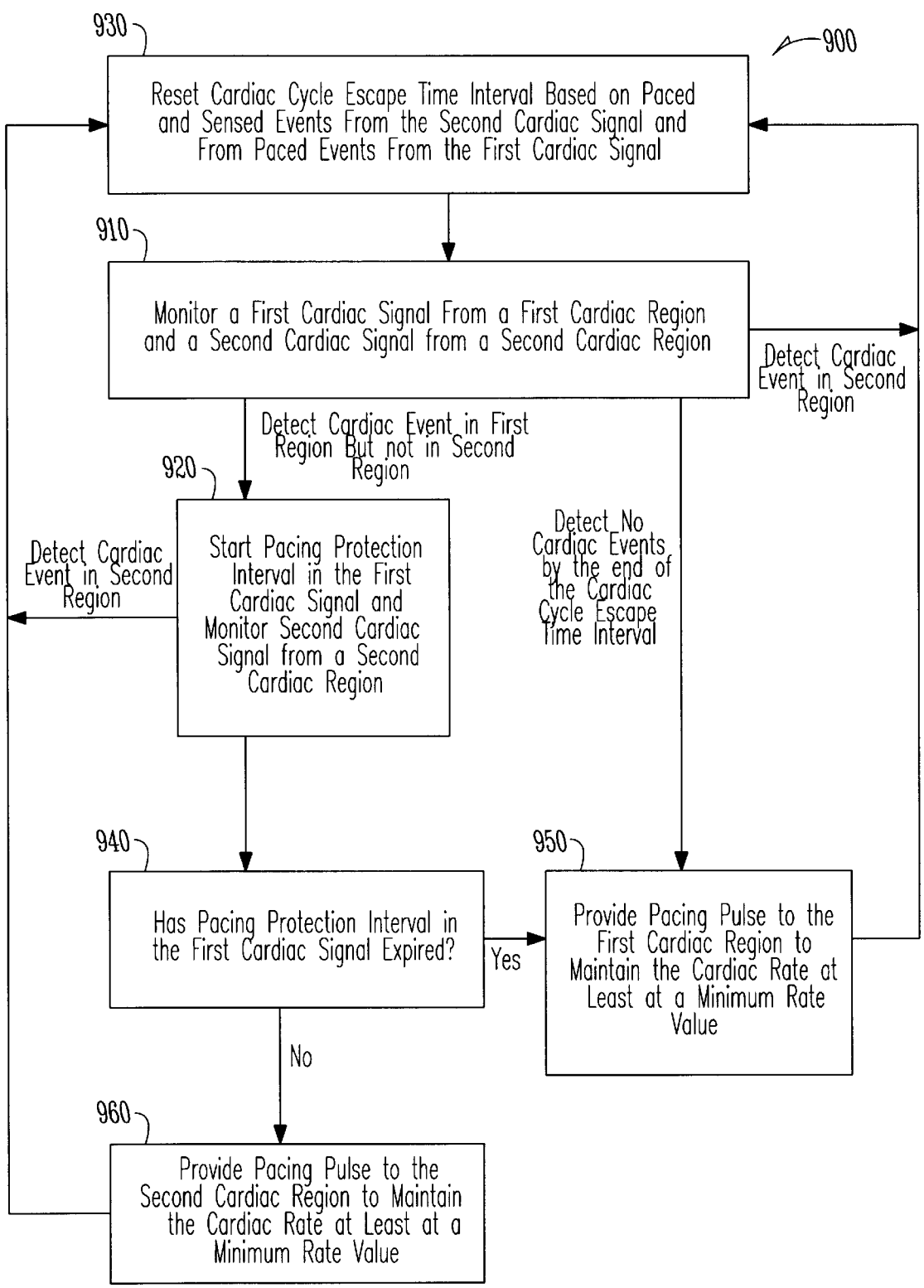
FIG. 9 is a flowchart showing one embodiment of the present subject matter.

FIG. 9 is a flow chart illustrating an additional embodiment of a method 900 according to the present subject matter. The method 900 starts at 910, where the first cardiac signal is monitored from the first cardiac region and the second cardiac signal is monitored from the second cardiac region. During the monitoring at 910, when a cardiac event is detected in the first cardiac region, but not in the second cardiac region the method 900 proceeds to 920 where the pacing protection interval is started for the first cardiac signal. Also at 920, the second cardiac signal continues to be monitored from the second cardiac region.

When a cardiac event is detected in the second cardiac signal from the second cardiac region, the method 900 proceeds to 930 where the cardiac cycle escape time interval is reset based on the sensed cardiac event from the second cardiac region. At 920, when no additional cardiac events are detected in the second cardiac signal by the end of the cardiac cycle escape time interval, the method 900 proceeds to 940. At 940, an inquiry as to whether the pacing protection interval in the first cardiac signal has expired is made. When the pacing protection interval in the first cardiac signal has expired, the method 900 proceeds to 950. At 950, the pacing pulse is provided to the first cardiac region to maintain the cardiac rate at at least the minimum rate value. The method 900 then proceeds to 930 where the cardiac cycle escape time interval is reset based on the pacing pulse provided to the first cardiac region. At 940, when the pacing protection interval in the first cardiac signal has not expired, the method 900 proceeds to 960. At 960, the pacing pulse is provided to the second cardiac region to maintain the cardiac rate at at least the minimum rate value. The method 900 then proceeds to 930 where the cardiac cycle escape time interval is reset based on the pacing pulse provided to the second cardiac region.

Referring again to 910, when no cardiac events are detected in the first or second cardiac signals by the end of the cardiac cycle escape time interval, the method 900 proceeds to 950. At 950, the pacing pulse is provided to the first cardiac region to maintain the cardiac rate at at least the minimum rate value. The method 900 then proceeds to 930 where the cardiac cycle escape time interval is reset based on the pacing pulse provided to the first cardiac region.

CONCLUSION

Although specific embodiments have been illustrated and described herein, it will be appreciated by those of ordinary skill in the art that any arrangement which is calculated to achieve the same purpose may be substituted for the specific embodiments shown. Many adaptations of the invention will be apparent to those of ordinary skill in the art. For example, use of markers or other display mechanisms to indicate reversion or the number of reversions may be used to assist the physician during interrogation of the cardiac rhythm management device. Different lead types, numbers of leads, and utilized heart chambers can be varied from the examples depicted herein. Accordingly, this application is intended to cover any adaptations or variations of the invention. It is manifestly intended that this invention be limited only by the following claims and equivalents thereof.

What is claimed is:

1. A method, comprising:
   sensing a first cardiac signal from a first cardiac region, where the first cardiac signal includes indications of cardiac events;
   sensing a second cardiac signal from a second cardiac region, where the second cardiac signal includes indications of cardiac events;
   determining a cardiac rate from the cardiac events in one of the first cardiac signal or the second cardiac signal;
   providing pacing pulses to the first cardiac region to maintain the cardiac rate at at least a minimum rate value;
   starting a pace protection interval for the first cardiac signal after a cardiac event in the first cardiac signal;
   inhibiting a pacing pulse to the first cardiac region during the pace protection interval; and
   providing the pacing pulse to the second cardiac region at a safety interval timed from the inhibited pacing pulse to the first cardiac region.

2. The method of claim 1, wherein providing the pacing pulse to the second cardiac region includes providing the pacing pulse to the second cardiac region to maintain the cardiac rate at at least the minimum rate value when the pace protection interval inhibits the pacing pulse to the first cardiac region.

3. The method of claim 1, including setting the safety interval timed from the inhibited pacing pulse in the range of zero (0.0) milliseconds to 300 milliseconds.

4. The method of claim 1, wherein providing the pacing pulse to the second cardiac region includes providing the pacing pulse to the second cardiac region after the pace protection interval.

5. The method of claim 1, wherein providing the pacing pulse to the second cardiac region includes providing the pacing pulse to the second cardiac region during the pace protection interval.

6. The method of claim 1, wherein sensing the first cardiac signal and the second cardiac signal includes detecting an intrinsic cardiac event;
   starting the pace protection interval in the first cardiac signal includes starting the pace protection interval in the first cardiac signal after the intrinsic cardiac event in the first cardiac signal;
   providing pacing pulses to the first cardiac region to maintain the cardiac rate at at least the minimum rate value includes starting a cardiac cycle escape time interval after the intrinsic cardiac event is sensed in the second cardiac signal;
   analyzing the second cardiac signal for a subsequent intrinsic cardiac event during the cardiac cycle escape time interval; and
   providing the pacing pulse to the second cardiac region at the safety interval timed from the inhibited pacing pulse to the first cardiac region includes providing the pacing pulse to the second cardiac site at the end of the cardiac cycle escape time interval when the subsequent intrinsic cardiac event is not detected in the second cardiac signal during the cardiac cycle escape time interval.

7. The method of claim 1, wherein sensing the first cardiac signal and the second cardiac signal includes identifying a paced cardiac event;
   starting the pace protection interval in the first cardiac signal includes starting the pace protection interval in the first cardiac signal after the paced cardiac event in the first cardiac signal;
   starting a cardiac cycle escape time interval after the paced cardiac event is identified in the first or second cardiac signal;
   analyzing the second cardiac signal for an intrinsic cardiac event during the cardiac cycle escape time interval; and
   providing the pacing pulse to the second cardiac region at the safety interval timed from the inhibited pacing pulse to the first cardiac region includes providing the pacing pulse to the second cardiac site at the end of the cardiac cycle escape time interval when the subsequent intrinsic cardiac event is not detected in the second cardiac signal during the cardiac cycle escape time interval.

8. The method of claim 1, wherein sensing the first cardiac signal includes sensing the first cardiac signal from a left ventricular chamber, and wherein sensing the second cardiac signal includes sensing the second cardiac signal from a right ventricular chamber.

9. The method of claim 1, wherein sensing the first cardiac signal includes sensing the first cardiac signal from a right ventricular chamber, and wherein sensing the second cardiac signal includes sensing the second cardiac signal from a left ventricular chamber.

10. The method of claim 1, wherein sensing the first cardiac signal includes sensing the first cardiac signal from a right atrial chamber, and wherein sensing the second cardiac signal includes sensing the second cardiac signal from a left atrial chamber.

11. The method of claim 1, wherein sensing the first cardiac signal includes sensing the first cardiac signal from a left atrial chamber, and wherein sensing the second cardiac signal includes sensing the second cardiac signal from a right atrial chamber.

12. The method of claim 1, wherein sensing the first cardiac signal includes sensing the first cardiac signal from the first cardiac region of a first cardiac chamber, and wherein sensing the second cardiac signal includes sensing the second cardiac signal from the second cardiac region of the first cardiac chamber.

13. The method of claim 1, including delivering a pacing pulse to a first chamber to maintain the cardiac rate at at least the minimum rate value when the pace protection interval does not inhibit the pacing pulse to the first cardiac chamber.

14. The method of claim 1, including programming the pace protection interval in a range of 200 milliseconds to 500 milliseconds.

15. An apparatus, comprising:
   a signal generator
   a first sensing/pacing electrode adapted for connection to the signal generator;
   a second sensing/pacing electrode adapted for connection to the signal generator; and
   where the signal generator includes:
      a first cardiac signal sensor to sense a first cardiac signal with the first sensing/pacing electrode;
      a second cardiac signal sensor to sense a second cardiac signal with the second sensing/pacing electrode;
      a cardiac signal analyzer, where the cardiac signal analyzer determines a cardiac rate from the cardiac events in one of the first cardiac signal or the second cardiac signal;

a pacing output, where the pacing output provides pacing pulses to the first sensing/pacing electrode to maintain a cardiac rate at at least a minimum rate value; and a pace protection circuit, wherein the pace protection circuit starts a pace protection interval for the first cardiac signal after a cardiac event in the first cardiac signal and where the pace protection circuit inhibits pacing pulses from the pacing output to a first cardiac chamber during the pace protection interval, and provides a pacing pulse from the pacing output to the second sensing/pacing electrode at a safety interval timed from the inhibited pacing pulse to the first cardiac chamber.

16. The apparatus of claim 15, wherein the pace protection circuit provides the pacing pulse to the second cardiac region to maintain the cardiac rate at at least the minimum rate value when the pace protection interval inhibits the pacing pulse to the first cardiac region.

17. The apparatus of claim 15, wherein the safety interval is programmed in the range of zero (0.0) milliseconds to 300 milliseconds.

18. The apparatus of claim 15, wherein the pace protection circuit provides the pacing pulse to the second cardiac region after the pace protection interval.

19. The apparatus of claim 15, wherein the pace protection circuit provides the pacing pulse to the second cardiac region during the pace protection interval.

20. The apparatus of claim 15, wherein the cardiac signal analyzer detects an intrinsic cardiac event in the first and second cardiac signals, the pace protection starts the pace protection interval in the first cardiac signal after the intrinsic cardiac event in the first cardiac signal and starts a cardiac cycle escape time interval after the intrinsic cardiac event is sensed in the second cardiac signal, and wherein the cardiac signal analyzer senses for a subsequent intrinsic cardiac event in the second cardiac signal during the cardiac cycle escape time interval, and the pace protection circuit provides a pacing pulse to the second sensing/pacing electrode at the end of the cardiac cycle escape time interval when the subsequent intrinsic cardiac event is not sensed by the cardiac signal analyzer from the second sensing/pacing electrode during the cardiac cycle escape time interval.

21. The apparatus of claim 15, wherein the cardiac signal analyzer identifies a paced cardiac event in the first and second cardiac signals, the pace protection starts the pace protection interval in the first cardiac signal after the paced cardiac event in the first cardiac signal and starts a cardiac cycle escape time interval after the paced cardiac event is identified in the first or second cardiac signal, and wherein the cardiac signal analyzer senses for an intrinsic cardiac event in the second cardiac signal during the cardiac cycle escape time interval, and the pace protection circuit provides a pacing pulse to the second sensing/pacing electrode at the end of the cardiac cycle escape time interval when the subsequent intrinsic cardiac event is not sensed by the cardiac signal analyzer from the second sensing/pacing electrode during the cardiac cycle escape time interval.

22. The apparatus of claim 15, wherein the first cardiac signal sensor senses a unipolar cardiac signal with the first sensing/pacing electrode, and the second cardiac signal sensor senses a unipolar cardiac signal with the second sensing/pacing electrode.

23. The apparatus of claim 15, wherein the first cardiac signal sensor senses a unipolar cardiac signal with the first sensing/pacing electrode, and the second cardiac signal sensor senses a bipolar cardiac signal with the second sensing/pacing electrode.

24. The apparatus of claim 15, wherein the first cardiac signal sensor senses a bipolar cardiac signal with the first sensing/pacing electrode, and the second cardiac signal sensor senses a bipolar cardiac signal with the second sensing/pacing electrode.

25. The apparatus of claim 15, wherein the pace protection circuit provides a pacing pulse to the first sensing/pacing electrode to maintain the cardiac rate at at least the minimum rate value when the pace protection circuit does not inhibit the pacing pulse to the first sensing/pacing electrode.

26. The apparatus of claim 15, wherein the pace protection interval is programmable in a range of 200 milliseconds to 500 milliseconds.

* * * * *